United States Patent [19]

Hung

[11] Patent Number: 4,967,022
[45] Date of Patent: Oct. 30, 1990

[54] PROCESS FOR FLUORINATED ALLENES

[75] Inventor: Ming-Hong Hung, Wilmington, Del.

[73] Assignee: E. I. du Pont de Nemours and Company, Wilmington, Del.

[21] Appl. No.: 442,676

[22] Filed: Nov. 29, 1989

[51] Int. Cl.$^5$ .................... C07C 17/26; C07C 17/30; C07C 21/18

[52] U.S. Cl. .................................. 570/136; 568/674; 568/685; 570/154

[58] Field of Search ................. 570/136; 568/674, 685

[56] References Cited

U.S. PATENT DOCUMENTS

| | | | |
|---|---|---|---|
| 2,733,278 | 1/1956 | Anderson | 570/136 |
| 3,300,540 | 1/1967 | Miller | 260/680 |
| 3,658,924 | 4/1972 | Haszeldine et al. | 570/136 |
| 3,901,948 | 8/1975 | Riess et al. | 570/136 |
| 4,618,734 | 10/1986 | Baum et al. | 570/136 |

OTHER PUBLICATIONS

R. N. Haszeldine et al., Journal of the Chemical Society, 2040 (1954).

D. J. Burton, "Advances in the Chemistry of Fluorine--Containing Organometallic Reagents", (Abstract).

P. L. Coe and N. E. Milner, Journal of Organometallic Chemistry, 70, 147 (1974).

V.C.R. McLaughlin and J. Thrower, Tetrahedron, vol. 25, pp. 5921–5940, Pergamon Press (1969).

*Primary Examiner*—J. E. Evans

[57] ABSTRACT

Processes for the preparation of perfluoroalkyl substituted allenes and novel bis-allenyl substituted perfluoroalkanes are disclosed.

4 Claims, No Drawings

PROCESS FOR FLUORINATED ALLENES

FIELD OF THE INVENTION

This invention relates to an improved process for the preparation of perfluoroalkyl substituted allenes, and novel bis-allenyl substituted perfluoroalkanes.

BACKGROUND OF THE INVENTION

U.S. Pat. No. 3,300,540 issued Jan. 24, 1967, discloses a process for the preparation of allenes comprising the reaction of a 3-halo-1-alkyne with a triorgano aluminum compound. The organo substituent in the aluminum compound is disclosed to be any group that does not deactivate the reagents, preferably hydrocarbon such as alkyl, cycloalkyl, aryl, aralkyl and cycloalky-alkyl. There is no disclosure nor suggestion that the organo substituent groups in the aluminum compound could bear fluorine atoms.

R. N. Haszeldine et al., Journal of the Chemical Society, 2040 (1954) disclose the preparation of 4,4,4-trifluorobuta-1,2-diene (alternate name 1-(perfluoromethyl)-1,2-propadiene) by the reaction of 4,4,4-trifluoro-2-iodobut-1-ene with ethanolic potassium hydroxide. There is no disclosure nor suggestion that this synthesis route would be applicable for the synthesis of higher members of the perfluoroalkyl substituted allene series.

An oral presentation by D. J. Burton entitled "Advances in the Chemistry of Fluorine-Containing Organometallic Reagents" at the American Chemical Society Ninth Winter Fluorine Conference, Jan. 29–Feb. 3, 1989, St., Petersburg, Fla., addressed the preparation, structure and synthetic utility of fluorine-containing organocadmium, organozinc and organocopper reagents.

P. L. Coe and N. E. Milner, Journal of Organometallic Chemistry, 70, 147(1974) disclosed the reaction of perfluoro-n-heptyl copper with propargyl bromide at 110° C. to be an extremely violent exothermic reaction that afforded, after a difficult workup that included a minor explosion, a 10% yield of 1-(perfluoro-n-heptyl)-1,2-propadiene. There is no disclosure nor suggestion relating to a means of performing said conversion in a safe, controllable, reproducible, high-yield manner.

Thus, there is a need for a suitable safe general synthetic route for the preparation of perfluoroalkyl substituted allenes, as well as for other intermediates useful in the production of fluorocarbon polymers.

It is therefore an object of the present invention to provide a controllable high yield process for the preparation of perfluoro substituted allenes.

It is a further object of the present invention to provide novel bis-allenyl substituted perfluoroalkane compounds.

It is a further object of the present invention to provide a process for the preparation of these novel diallenic compounds.

SUMMARY OF THE INVENTION

This invention provides an improved process for the preparation of compounds represented by the formula (I):

$$R_f-CH=C=CH_2$$

wherein:

$R_f$ is a primary perfluorocarbyl substituent group containing up to about 20 carbon atoms and which may contain ether oxygen linkages comprising:

(a) reacting a primary perfluorocarbyl halide of formula $R_f-X$, wherein $R_f$ is defined as above and X may be bromine or iodine, with copper powder to yield a primary perfluorocarbyl copper reagent $R_f-Cu$; and (b) reacting said primary perfluorocarbyl copper reagent with a propargyl halide $HC\equiv CCH_2Y$ where Y may be chlorine, bromine, or iodine at temperatures below about 50° C. in a polar aprotic solvent and isolating the product from the reaction mixture.

This invention also provides novel bis-allenic compounds represented by the structure of formula (II):

$$H_2C=C=CH-R_f'-CH=C=CH_2,$$

wherein:

$R_f'$ is a diprimary disubstituted perfluorocarbyl radical containing up to about 20 carbon atoms and which may contain ether oxygen linkages.

This invention also provides a process for the manufacture of the diallenic compounds of formula (II) comprising (a) reacting a diprimary perfluorocarbyl dihalide represented by the structure $X-R_f'-X$ where $R_f'$ and X are defined as above with copper powder to yield a diprimary perfluorocarbyl dicopper reagent, $Cu-R_f'-Cu$, b) reacting said dicopper reagent with a propargyl halide $HC\equiv CCH_2Y$ where Y may be chlorine, bromine or iodine at temperatures below about 50° C. in a polar aprotic solvent; and (c) isolating the product from the reaction mixture.

DETAILED DESCRIPTION OF THE INVENTION

The compounds provided by the present invention are useful as intermediates in the preparation of further fluorine containing compounds or as monomers for incorporation into fluorine containing polymers.

The present invention comprises an improved process for the preparation of compounds of formula (I):

$$R_f-CH=C=CH_2 \qquad (I)$$

wherein:

$R_f$ is a primary perfluorocarbyl substituent group containing up to about 20 carbon atoms and which may contain ether oxygen linkages. Said process comprises the steps:

(a) reacting a primary perfluorocarbyl halide of formula $R_f-X$, wherein $R_f$ is defined as in formula (I) and X is bromine or iodine, with copper powder to yield a primary perfluorocarbyl copper reagent $R_f-Cu$;

(b) reacting said primary perfluorocarbyl copper reagent with a propargyl halide, $HC\equiv CCH_2Y$, wherein Y is chlorine, bromine, or iodine to yield the desired compound of formula (I); and (c) isolating the desired compound of formula (I) from the reaction mixture.

$R_f$, in the formulae $R_f-CH=C=CH_2$, $R_f-X$ and $R_f-Cu$ is a primary perfluorocarbyl substituent group containing up to about 20 carbon atoms and which may contain ether oxygen linkages. Preferably $R_f$ is of the formula $C_nF_{2n+1}$, where n is 1 to 12. Most preferably n in the above formula is an even integer from 2 to 12.

In the first step of the process of this invention, the primary perfluorocarbyl halide, $R_f$—X is reacted with copper powder. The copper powder employed in this work was high-purity, 99.995%, copper. Less pure copper powder can be used in the process of this invention. For the sake of ease of operation, high-purity copper powder is preferred. About 1 to about 3 equivalents of copper powder per equivalent of primary perfluorocarbyl halide compound can be used; the use of two equivalents is preferred.

The primary perfluorocarbyl compound and the copper powder are allowed to react in the presence of a essentially water-free, preferably anhydrous aprotic polar solvent, for example, dimethyl sulfoxide, dimethylformamide, or n-methylpyrolidone. The use of dimethyl sulfoxide is preferred. The reaction to form the primary perfluorocarbyl copper reagent is carried out at a temperature of about 100° C. to about 130° C. Preferably the reaction is carried out at about 110° C. to about 120° C. The time of the reaction is from about 30 minutes to about 3 hours; the preferred reaction time is about 1 hour.

The reaction is carried out under an inert gas atmosphere. Nitrogen, helium or argon gas may be employed. Argon is preferred. It is preferable that the reaction be carried out with agitation. The reaction is preferably carried out at normal atmospheric pressure. After the above described reaction conditions have been carried out, the primary perfluorocarbyl copper reagent is ready for use.

To a solution of the primary perfluorocarbyl copper reagent dissolved in an essentially water-free, preferably anhydrous polar aprotic solvent which may be, for example, dimethyl sulfoxide, dimethylformamide or n-methylpyrolidone, and which preferably is dimethyl sulfoxide, the propargyl halide is added slowly. The halide substituent on the propargyl group may be chloride, bromide or iodide. Bromide is preferred. It is preferred to use equimolar amounts of the primary perfluorocarbyl copper reagent and the propargyl halide. The controlling factor for the propargyl halide addition rate is temperature control of the exothermic reaction. The rate of the propargyl halide addition is adjusted so that the temperature, which is optionally being maintained by a source of cooling, does not deviate from a predetermined desired temperature range. The temperature range may be from about 10° C. to about 50° C.; the preferred temperature range is from about 15° C. to about 20° C.

Depending on the heat-removing capacity of the cooling source and the scale of the reaction, the time of propargyl halide addition may be from about 10–15 minutes up to about 1 hour or longer. The reaction is carried out under an inert gas atmosphere. Nitrogen, helium or argon gas may be employed. Argon is preferred. It is preferable that the reaction be carried out with agitation. The reaction is preferably carried out at normal atmospheric pressure. Once all the propargyl halide has been added, product compound of formula (I) should be isolated expeditiously.

Product isolation may begin essentially immediately, but may be delayed, with some loss of yield, overnight. It is preferred that isolation commence essentially immediately. Various methods may be used for isolation of product from the reaction mixture. Product may be distilled from the reaction mixture, optionally at reduced pressure. Product may be separated from the reaction mixture by means of liquid-liquid extraction by introducing a second solvent, in which the product is soluble and which is not totally miscible with the original reaction solvent, into the reaction system and then separating the two resulting liquid phases and proceeding to obtain product from the product-bearing solvent phase employing means known to one skilled in the art, for example removal of the solvent under vacuum followed by distillation of product.

In a second aspect the present invention relates to novel bis-allenic compounds represented by the structure of formula (II):

$$H_2C=C=CH-R_f'-CH=C=CH_2 \qquad (II)$$

wherein:

$R_f'$ is a diprimary disubstituted perfluorocarbyl radical containing up to about 20 carbon atoms and which may contain ether oxygen linkages.

Preferably $R_f'$ is of the formula $C_nF_{2n}$, where n is 3 to 12. Such compounds are useful as intermediates in the preparation of further fluorine containing compounds or as monomers for incorporation into fluorine containing polymers.

In a third aspect, the present invention relates to use of the above described process to prepare the bis-allenic compounds of formula (II). Said process comprises (a) reacting a diprimary perfluorocarbyl dihalide represented by the structure X—$R_f'$—X wherein X is bromine or iodine and $R_f'$ is as defined above in formula (II) with copper powder to yield a diprimary perfluorocarbyl dicopper reagent, Cu—$R_f'$—Cu; (b) reacting said dicopper reagent with a propargyl halide, HC≡CCH$_2$Y wherein Y is chlorine, bromine or iodine at temperatures below about 50° C. in a polar aprotic solvent to yield a compound of formula (II); and (c) isolating the compound of formula (II) from the reaction mixture.

For the formation of the intermediate dicopper reagent, 2 to 6 equivalents of copper powder per mole of diprimary perfluorocarbyl dihalide are employed in reaction step (a), and the preferred temperature range is from about 80° C. to about 120° C. with from about 90° C. to about 110° C. being most preferred. Other conditions are as previously described for the preparation of compounds of formula (I).

In the examples that follow, the anhydrous dimethyl sulfoxide was used as purchased from Aldrich Chemical Co., Milwaukee, Wis. Copper powder (99.995%), was purchased from Aldrich. The perfuoroalkyl halides and propargyl bromide were commercially available products and were used as obtained.

EXAMPLE 1

Preparation of $C_8F_{17}CH=C=CH_2$

To a stirred suspension of copper powder (12.7 g, 0.2 mole) in 100 ml of dimethyl sulfoxide (DMSO), perfluoro-n-octyl iodide (54.6 g 0.1 mole) was added. The suspension was heated to 120° C. and kept at 115° C. to 120° C. for 1 hour, during which time the solution turned chocolate brown and then orange. The perfluorooctyl copper reagent was cooled to 15° C., and the addition of propargyl bromide (12 g, 0.1 mole) as a 80 weight percent solution in toluene (i.e., 15 g of an 80 weight percent solution) was begun. The reaction was very exothermic initially and then moderated. When the addition was complete, the reaction mixture was agitated overnight at room temperature. The product was flash-distilled from the reaction mixture, and the crude product was purified by vacuum distillation: 27.0 g, 59% yield, of a clear colorless liquid was obtained. b.p. 86° C.–90° C. at 50 mm Hg.

$^1$H NMR:(CDCl$_3$): δ5.30 (m, 1H), 5.18 (m, 2H); $^{19}$F NMR(CDCl$_3$): −82.1 (tm, J=8.4 Hz, 3F), −119.2 (s, br, 2F), −122.3 (br, 6F), −123.3 (s, br, 2F), −124.0 (s, br, 2F), −127.0 (s, br, 2F).

EXAMPLE 2

Preparation of C$_8$F$_{17}$CH=C=CH$_2$

The perfluoro-n-octyl copper reagent was prepared on a 0.1 mole scale essentially as in Example 1 at a reaction temperature of 110° C. to 115° C. To the cooled organocopper reaction mixture, propargyl bromide (11.9 g, 0.1 mole) was added while maintaining the temperature at 15° C. to 20° C. After the addition, the reaction mixture was stirred for 20 minutes at 15° C. Product was removed by flash distillation as before, and purified by vacuum distillation. There were obtained 34.0 g, (74.2% yield).
b.p. 86° C.–90° C./50 mm Hg.

EXAMPLE 3

Preparation of C$_6$F$_{13}$CH=C=CH$_2$ n-(Perfluoro)hexyl iodide (44.6 g, 0.1 mole) was converted to n-(perfluoro)hexyl allene by a procedure essentially the same as in Example 1. The product (23.0 g, 64% yield) was obtained as a clear colorless oil.
b.p. 88° C.–90° C./100 mm Hg.
$^1$H NMR (CDCl$_3$) δ5.36 (m, 1H), 5.20 (m, 2H).

EXAMPLE 4

Preparation of C$_6$F$_{13}$CH=C=CH$_2$

To a stirred suspension of copper powder (12.7 g, 0.2 mole) in 100 ml of dimethyl sulfoxide (DMSO), perfluoro-n-hexyl iodide (44.6 g, 0.1 mole) was added. The suspension was heated to 120° C. and kept at 115° C. to 120° C. for 1 hour, during which time the solution turned chocolate brown and then orange. The perfluorohexyl copper reagent was cooled to 15° C., and the addition of propargyl bromide (12 g, 0.1 mole) was begun. The reaction was somewhat exothermic. When the addition was complete, the reaction mixture was agitated for 20 minutes at 15° C. before flash distillation at 50° C. to 75° C./50-60 mm Hg. The crude product was purified by vacuum distillation to a clear colorless oil.
b. p. 64° C./50-55 mm Hg.
Yield: 20.0 g, 56%.

A repetition of this preferred procedure using essentially the same technique afforded the same product, 26.5 g, in 74% yield. Reasons for the lower yield in the first attempt were not apparent.

EXAMPLE 5

Preparation of H$_2$C=C=CHC$_6$F$_{12}$CH=C=CH$_2$

Perfluoro-1,6-diiodo-n-hexane (27.7 g, 0.05 mole) was mixed with copper powder (12.7 g, 0.20 mole) in 60 ml of dimethyl sulfoxide and the mixture was heated to 80° C. The solution color turned to orange and then dark. The mixture was heated to 95° C. to 100° C. and held at that temperature for 1 hour, then cooled to 15° C. to 20° C. Propargyl bromide (11.9 g, 0.10 mole) was added slowly via syringe. The reaction was exothermic; external cooling was employed to keep the temperature in the range of 15° C. to 20° C. After the addition of propargyl bromide was complete, ether was added to the reaction mixture with agitation. The ether was decanted. This ether extraction cycle was repeated three times. All ether extracts were combined and evaporated under vacuum. The residue was distilled under vacuum to give the desired product (5.0 g, 26% yield).
b.p. 90° C./12 mm Hg.
$^1$H NMR(CDCl$_3$): δ5.44 (m,2H), 5.30 (dd, J=5.6, 12.1 Hz, 4H); $^{19}$F NMR(CDCl$_3$): −108.9 (quintet, J=4.9 Hz, 4F), −122.1 (m, 4F), −124.0 (m, 4F).

What is claimed is:

1. A compound comprising formula (II):

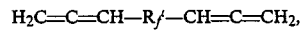

H$_2$C=C=CH—R$_f'$—CH=C=CH$_2$, wherein
   R$_f'$ is a diprimary disubstituted perfluorocarbyl radical up to about 20 carbon atoms which can contain one or more ether oxygen linkages.

2. A compound of claim 1 wherein R$_f'$ is C$_n$F$_{2n}$, wherein n is from about 3 to about 20.

3. A compound of claim 2 wherein n is 4, 6, 8, 10 or 12.

4. A compound of claim 3 which is H$_2$C=C=CHC$_6$F$_{12}$CH=C=CH$_2$.

* * * * *